(12) United States Patent
Shimizu et al.

(10) Patent No.: US 9,115,071 B2
(45) Date of Patent: Aug. 25, 2015

(54) PROCESS FOR PRODUCING ACETIC ACID

(75) Inventors: Masahiko Shimizu, Tokyo (JP); Ryuji Saito, Otake (JP); Hiroyuki Miura, Himeji (JP)

(73) Assignee: DAICEL CORPORATION, Osaka-Shi (JP)

( * ) Notice: Subject to any disclaimer, the term of this patent is extended or adjusted under 35 U.S.C. 154(b) by 145 days.

(21) Appl. No.: 13/994,373

(22) PCT Filed: Dec. 1, 2011

(86) PCT No.: PCT/JP2011/077844
§ 371 (c)(1),
(2), (4) Date: Jun. 14, 2013

(87) PCT Pub. No.: WO2012/081416
PCT Pub. Date: Jun. 21, 2012

(65) Prior Publication Data
US 2013/0310603 A1 Nov. 21, 2013

(30) Foreign Application Priority Data
Dec. 15, 2010 (JP) .................. 2010-279797

(51) Int. Cl.
C07C 51/12 (2006.01)

(52) U.S. Cl.
CPC ..................... C07C 51/12 (2013.01)

(58) Field of Classification Search
None
See application file for complete search history.

(56) References Cited

U.S. PATENT DOCUMENTS

| | | | |
|---|---|---|---|
| 4,994,608 | A | 2/1991 | Torrence et al. |
| 5,391,821 | A | 2/1995 | Koyama et al. |
| 5,672,744 | A | 9/1997 | Kagotani et al. |
| 5,877,348 | A | 3/1999 | Ditzel et al. |
| 2008/0097124 | A1 | 4/2008 | Kojima |
| 2008/0214866 | A1 | 9/2008 | Miura et al. |
| 2009/0082593 | A1 | 3/2009 | Kojima |
| 2013/0116470 | A1 | 5/2013 | Miura et al. |

FOREIGN PATENT DOCUMENTS

| | | | |
|---|---|---|---|
| JP | 62-298549 | A | 12/1987 |
| JP | 5-140024 | A | 6/1993 |
| JP | 7-330657 | A | 12/1995 |
| JP | 8-277244 | A | 10/1996 |
| JP | 10-310550 | A | 11/1998 |
| JP | 2005-529178 | A | 9/2005 |
| JP | 2006-160645 | A | 6/2006 |
| JP | 2006-199681 | A | 8/2006 |
| JP | 2009-501129 | A | 1/2009 |
| JP | 2012-46490 | A | 3/2012 |
| WO | WO 03/106396 | A1 | 12/2003 |
| WO | WO 2007/007891 | A2 | 1/2007 |
| WO | WO 2007/040087 | A1 | 4/2007 |

OTHER PUBLICATIONS

International Preliminary Report on Patentability and Written Opinion of the International Searching Authority (Forms PCT/IB/338, PCT/IB/373 and PCT/ISA/237) for International Application No. PCT/JP2011/077844, dated Jun. 27, 2013.

*Primary Examiner* — Yevegeny Valenrod
(74) *Attorney, Agent, or Firm* — Birch, Stewart, Kolasch & Birch, LLP

(57) ABSTRACT

Acetic acid is produced while inhibiting an increased concentration or production of hydrogen iodide in a carbonylation reactor or corrosion of the carbonylation reactor.
A production process of acetic acid comprises a reaction step for continuously allowing methanol to react with carbon monoxide in the presence of a catalyst system comprising a metal catalyst (e.g., a rhodium catalyst), an ionic iodide (e.g., lithium iodide), and methyl iodide in a carbonylation reactor; and in the process, (i) the concentration of the metal catalyst is maintained at not less than 860 ppm on the basis of weight, the concentration of water is maintained at 0.8 to 15% by weight, the concentration of methyl iodide is maintained at not more than 13.9% by weight, and the concentration of methyl acetate is maintained at not less than 0.1% by weight, in a whole liquid phase in the reactor, and/or (ii) the concentration of the metal catalyst is maintained at not less than 660 ppm on the basis of weight, the concentration of water is maintained at 0.8 to 3.9% by weight, the concentration of the ionic iodide is maintained at not more than 13% by weight, the concentration of methyl iodide is maintained at not more than 13.9% by weight, and the concentration of methyl acetate is maintained at not less than 0.1% by weight, in a whole liquid phase in the reactor.

10 Claims, 1 Drawing Sheet

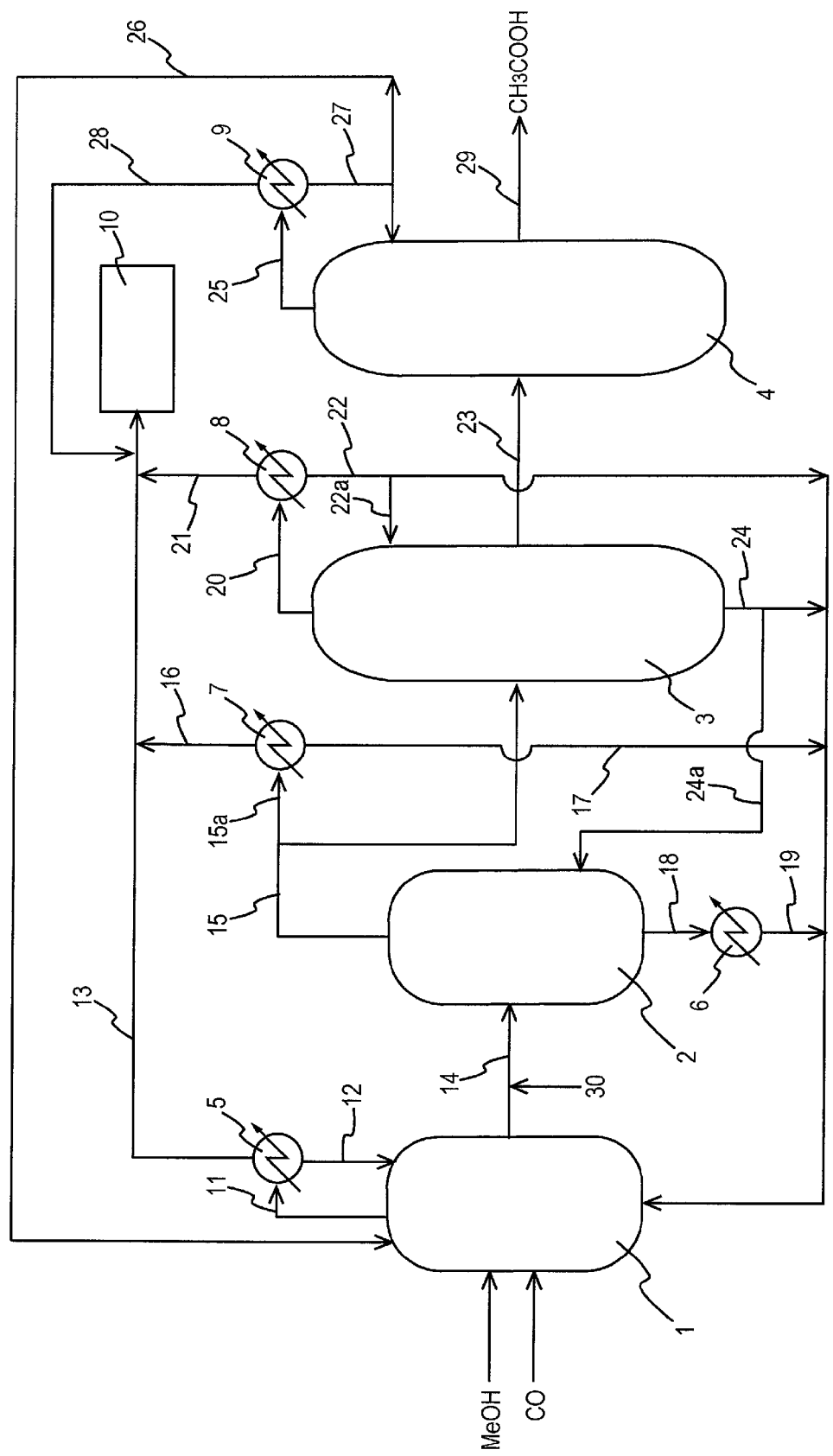

PROCESS FOR PRODUCING ACETIC ACID

TECHNICAL FIELD

The present invention relates to a process for producing acetic acid while inhibiting production (or an increase in concentration) of hydrogen iodide in a carbonylation reaction of methanol with carbon monoxide (or a carbonylation reactor for a reaction of methanol with carbon monoxide) or corrosion of the carbonylation reactor.

BACKGROUND ART

Various industrial production processes of acetic acid have been known. Among others, an industrially excellent process includes a process which comprises continuously allowing methanol to react with carbon monoxide with the use of a metal catalyst (such as a rhodium catalyst), an ionic iodide (e.g., lithium iodide), and methyl iodide in the presence of water in a carbonylation reactor to give acetic acid. In this process, usually, acetic acid is produced as follows: a reaction mixture of methanol and carbon monoxide, which contains acetic acid, is subjected to a distillation (a flash distillation) in a flasher (a flash evaporator), and a component vaporized by the distillation is subjected to a further distillation to separate (further purify) a component containing acetic acid.

The reaction mixture contains hydrogen iodide in addition to product acetic acid, ionic iodide, and methyl iodide. An increased concentration of hydrogen iodide inside the carbonylation reactor may precipitate the corrosion of the carbonylation reactor. Moreover, when the reaction mixture containing hydrogen iodide is subjected to the flasher or a further distillation column for separating acetic acid, or when a residue (liquid residue or bottom fraction) after the separation of the vaporized component is recycled to the reactor, the reaction system may be adversely affected, and additionally the corrosion of peripheral device(s) may be precipitated.

Therefore, in the production process of acetic acid, it is preferable that rising of the concentration of hydrogen iodide in the carbonylation reactor (or the reaction mixture) be prevented. Although a technique for inhibiting condensation of hydrogen iodide in a distillation column such as plate column, packed column has been already known, a technique closely focused on hydrogen iodide in a carbonylation reactor is not known.

For example, Japanese Patent Application Laid-Open No. 2006-160645 (JP-2006-160645A, Patent Document 1) discloses a process for distilling a mixture containing hydrogen iodide and water, which comprises distilling the mixture having a water content of not more than 5% by weight in a distillation system to prevent condensation of hydrogen iodide in the distillation system. In Examples of this document, a process solution (specifically, a volatile component separated by a flash distillation of a reaction mixture) free from an ionic iodide (such as lithium iodide) is examined for the effect of the water concentration on the hydrogen iodide condensation. Incidentally, the document discloses a wide range of compositions (or formulations) of the mixture (for example, the concentration of water is about 0.1 to 14% by weight, the proportion of a carbonylation catalyst is about 50 to 5000 ppm, the iodide salt content is about 0.1 to 40% by weight, the concentration of an alkyl iodide is about 1 to 25% by weight, the concentration of a carboxylate ester is about 0.1 to 20% by weight). However, the document is silent on any relationship between the composition of these components and hydrogen iodide in the carbonylation reactor.

As described above, the purpose of the conventional art is to condense hydrogen iodide in distillation, and the decrease of hydrogen iodide in a carbonylation reactor has not been examined.

RELATED ART DOCUMENTS

Patent Documents

Patent Document 1: JP-2006-160645A (Claims, Paragraph Nos. [0020] to [0021], and Examples)

SUMMARY OF THE INVENTION

Problems to be Solved by the Invention

It is therefore an object of the present invention to provide a process for producing acetic acid while efficiently inhibiting (or preventing) an increase in a concentration of hydrogen iodide in a carbonylation reactor (or in a reaction mixture) or corrosion of the carbonylation reactor.

It is another object of the present invention to provide a process for producing acetic acid, the process preventing hydrogen iodide production in a carbonylation reactor (or in a reaction mixture) or corrosion of the carbonylation reactor while maintaining highly efficient production of acetic acid.

It is still another object of the present invention to provide process for producing acetic acid, the process preventing hydrogen iodide production in a carbonylation reactor or corrosion of the carbonylation reactor while promoting energy-saving.

It is a further object of the present invention to provide a process for producing acetic acid, the process preventing corrosion of a carbonylation reactor or succeeding process (es) or apparatus (e.g., a flash evaporator and a distillation column).

Means to Solve the Problems

The production of hydrogen iodide in a carbonylation reactor theoretically depends on reaction conditions such as a reaction temperature, a pressure, and a composition (or formulation) of each component. The inventors of the present invention examined a method for inhibiting an increase in hydrogen iodide concentration in a carbonylation reaction based on the information of such an equilibrium theory. However, the temperature or the pressure can be established arbitrarily, and the combination thereof variously changes the reaction conditions. In addition, there are a variety of reactions involved in the production of hydrogen iodide in the carbonylation reaction, and these reactions are complicated. Therefore, it was actually difficult to stably inhibit the production of hydrogen iodide and the increase in hydrogen iodide concentration, while maintaining sufficiently efficient production of acetic acid, based on a simple equilibrium theory. Moreover, the corrosion of the carbonylation reactor seems to be influenced by not only the concentration of hydrogen iodide in the carbonylation reactor but also other conditions. Thus a simple decrease in hydrogen iodide concentration sometimes failed to inhibit the corrosion of the carbonylation reactor efficiently.

The inventors of the present invention made intensive studies to achieve the above objects and finally found that the production or increased concentration of hydrogen iodide in the reaction mixture or in the carbonylation reactor is inhibited while ensuring sufficiently efficient production of acetic acid by carrying out the carbonylation reaction with the composition of each component stringently controlled or selected; that the inhibition of the increase in hydrogen iodide concentration prevents the corrosion of the carbonylation reactor and further reduces adverse effects (e.g., corrosion) caused by hydrogen iodide on step(s) or apparatus to be established following the carbonylation reactor [for example, a flash evaporator; a distillation column for subjecting a volatile component to a further distillation, or incidental facilities (or equipment) thereof (e.g., a heat exchanger such as a circulating pump, a condenser, or a reboiler); incidental facilities (or equipment) for recycling a liquid catalyst mixture to a reactor (e.g., a heat exchanger and a circulating pump); and feed lines for these flash evaporator, distillation column, and incidental facilities]. The present invention was accomplished based on the above findings.

That is, the process of the present invention includes a process for producing acetic acid, which comprises a reaction step for continuously allowing methanol to react with carbon monoxide in the presence of a catalyst system comprising a metal catalyst (e.g., a rhodium catalyst), an ionic iodide (an alkali metal iodide such as lithium iodide), and methyl iodide in a carbonylation reactor (specifically, a reaction step for allowing methanol to react with carbon monoxide to produce acetic acid), wherein, in the reaction step, (i) the concentration of the metal catalyst is maintained at not less than 860 ppm on the basis of weight, the concentration of water is maintained at 0.8 to 15% by weight, the concentration of methyl iodide is maintained at not more than 13.9% by weight, and the concentration of methyl acetate is maintained at not less than 0.1% by weight, in a whole liquid phase in the reactor, and/or (ii) the concentration of the metal catalyst is maintained at not less than 660 ppm on the basis of weight, the concentration of water is maintained at 0.8 to 3.9% by weight, the concentration of the ionic iodide is maintained at not more than 13% by weight, the concentration of methyl iodide is maintained at not more than 13.9% by weight, and the concentration of methyl acetate is maintained at not less than 0.1% by weight, in a whole liquid phase in the reactor.

The process (i) (sometimes referred to as a first process, a first embodiment, or others) and/or the process (ii) (sometimes referred to as a second process, a second embodiment, or others) efficiently inhibits (or prevents) the production of hydrogen iodide in the carbonylation reactor. According to the process of the present invention, highly efficient production of acetic acid is ensured in spite of inhibition of the production or increased concentration of hydrogen iodide. For example, in the process (i) the production rate (or formation rate) of acetic acid (reaction rate, production rate of acetic acid in the reaction step) may be about not less than 10 mol/L·h (particularly about not less than 19 mol/L·h), or in the process (ii) the production rate of acetic acid may be about not less than 5 mol/L·h. Moreover, in the process (ii) also achieves energy-saving by regulating the concentration of water to not more than 0.8 to 3.9% by weight.

For the first process, in the liquid phase in the reactor, the concentration of the metal catalyst may be maintained at about 860 to 5000 ppm on the basis of weight, the concentration of water may be maintained at about 0.8 to 15% by weight, the concentration of the ionic iodide may be maintained at about not more than 25% by weight, and the concentration of methyl iodide may be maintained at about 2 to 13.9% by weight.

For a representative example of the first process, the production rate of acetic acid may be about 10 to 45 mol/L·h (e.g., about 12 to 35 mol/L·h, and preferably about 19 to 35 mol/L·h), and in the liquid phase in the reactor, the concentration of the metal catalyst may be maintained at about 880 to 3000 ppm (e.g., about 900 to 1500 ppm) on the basis of weight, the concentration of water may be maintained at about 1 to 10% by weight (e.g., about 1.5 to 9% by weight), the concentration of the ionic iodide may be maintained at about 0.5 to 25% by weight (e.g., about 2 to 20% by weight), the concentration of methyl iodide may be maintained at about 4 to 13.5% by weight (e.g., about 5 to 13% by weight, and preferably about 6 to 13% by weight), and the concentration of methyl acetate may be maintained at about not less than 0.5% by weight (e.g., about not less than 1% by weight).

For the second process, in the liquid phase in the reactor, the concentration of the metal catalyst may be maintained at about 660 to 5000 ppm on the basis of weight, the concentration of water may be maintained at about 1 to 3.5% by weight, the concentration of the ionic iodide may be maintained at about 0.5 to 13% by weight, and the concentration of methyl iodide may be maintained at about 2 to 13.9% by weight.

For a representative example of the second process, the production rate of acetic acid may be about 5 to 45 mol/L·h (e.g., about 7 to 35 mol/L·h), and in the liquid phase in the reactor, the concentration of the metal catalyst may be maintained at about 700 to 3000 ppm (e.g., about 800 to 1500 ppm) on the basis of weight, the concentration of water may be maintained at about 1.5 to 3% by weight (e.g., about 2 to 2.8% by weight), the concentration of the ionic iodide may be maintained at about 1 to 12% by weight (e.g., about 2 to 11% by weight), the concentration of methyl iodide may be maintained at about 3 to 12% by weight (e.g., about 4 to 11% by weight), and the concentration of methyl acetate may be maintained at about not less than 0.5% by weight (e.g., about not less than 1% by weight).

Moreover, according to the process of the present invention, the reaction may be conducted while maintaining a carbon monoxide pressure (partial pressure) of not less than 900 kPa and a hydrogen pressure (partial pressure) of not less than 4 kPa in the reactor.

It is sufficient that the process of the present invention for producing acetic acid comprises at least the above-mentioned reaction step. The process usually comprises a flash distillation step for continuously feeding a flasher with a reaction mixture from the reactor to evaporate a volatile component by a flash distillation, the volatile component at least containing product acetic acid, methyl acetate, and methyl iodide; and an acetic acid collection step for separating a stream containing acetic acid from the volatile component and collecting acetic acid. According to the present invention, since the concentration of hydrogen iodide in the reaction mixture can be reduced, production or increased concentration of hydrogen iodide can be inhibited (or prevented) in these steps to be established following the reaction step. For example, in the flash distillation step, the reaction mixture may be separated into the volatile component and a liquid catalyst mixture (bottom fraction) at least containing the metal catalyst and the ionic iodide, and the concentration of hydrogen iodide may be maintained at not more than 1% by weight on the basis of weight in the liquid catalyst mixture.

For the process comprising such a flash distillation step, in the flash distillation step, the volatile component may be separated from the reaction mixture, and the flash distillation may be conducted under the condition that the concentration of methyl acetate is not less than 0.6% in the liquid catalyst mixture at least containing the metal catalyst and the ionic iodide. The flash distillation under such a condition further advantageously inhibits the increase in the concentration of hydrogen iodide in the flash evaporator.

The concentration of methyl acetate in the liquid catalyst mixture may be not less than 1.5% by weight (particularly, not less than 2% by weight). Moreover, the concentration of water in the liquid catalyst mixture may be not more than 15% by weight, the concentration of the metal catalyst in the liquid catalyst mixture may be not less than 300 ppm on the basis of weight. Further, in the liquid catalyst mixture, the concentration of acetic acid may be not less than 40% by weight.

Representatively, with respect to the concentration of each component in the liquid catalyst mixture, the concentration of the ionic iodide may be not more than 50% by weight, the concentration of methyl iodide may be not more than 5% by weight, the concentration of acetic acid may be about 45 to 90% by weight, and the concentration of water may be not more than 10% by weight. In particular, with respect to the concentration of each component in the liquid catalyst mixture, the concentration of the ionic iodide may be not more than 40% by weight, the concentration of methyl iodide may be about 0.01 to 4% by weight, the concentration of acetic acid may be about 50 to 85% by weight, the concentration of methyl acetate may be about 0.7 to 5% by weight, and the concentration of water may be about 0.8 to 8% by weight.

In the flash distillation step, the flash distillation may be carried out at an absolute pressure of 0.1 to 0.5 MPa, and the temperature (or flash distillation temperature) in the liquid catalyst mixture may be about 100 to 170° C.

In the process of the present invention, the concentration of each component in the flash evaporator may be adjusted by adding each component or component(s) for producing each component. For example, the concentration of methyl acetate in the liquid catalyst mixture may be adjusted (for example, adjusted to not less than 0.6% by weight) by adding or mixing methyl acetate and/or a component producing methyl acetate to the reaction mixture and/or the flash evaporator.

According to the present invention, as described above, stringent control of each component concentration in the carbonylation reactor can prevent (or inhibit) the increased concentration or production of hydrogen iodide in the carbonylation reactor (further, the succeeding step(s) such as the flash distillation step), and then can efficiently prevent (or inhibit) the corrosion of the carbonylation reactor or step(s) or apparatus to be established following the carbonylation reactor.

Thus, the present invention also includes a method for inhibiting corrosion of a carbonylation reactor in a production process of acetic acid, the production process comprising a reaction step for continuously allowing methanol to react with carbon monoxide in the presence of a catalyst system comprising a metal catalyst, an ionic iodide, and methyl iodide in the carbonylation reactor, wherein, in the reaction step, (i) the concentration of the metal catalyst is maintained at not less than 860 ppm on the basis of weight, the concentration of water is maintained at 0.8 to 15% by weight, the concentration of methyl iodide is maintained at not more than 13.9% by weight, and the concentration of methyl acetate is maintained at not less than 0.1% by weight, in a whole liquid phase in the reactor, and/or (ii) the concentration of the metal catalyst is maintained at not less than 660 ppm on the basis of weight, the concentration of water is maintained at 0.8 to 3.9% by weight, the concentration of the ionic iodide is maintained at not more than 13% by weight, the concentration of methyl iodide is maintained at not more than 13.9% by weight, and the concentration of methyl acetate is maintained at not less than 0.1% by weight, in a whole liquid phase in the reactor.

Such a method not only prevents the production or increased concentration of hydrogen iodide or the corrosion of the carbonylation reactor but also achieves a highly efficient production of acetic acid. For example, in the process (i) the production rate of acetic acid may be about not less than 10 mol/L·h, and in the process (ii) the production rate of acetic acid may be about not less than 5 mol/L·h.

In the process or method of the present invention, the material of the carbonylation reactor (further the flasher) may comprise an alloy (for example, a nickel-based alloy). The present invention achieves the inhibition of the corrosion, and even a carbonylation reactor made of such a relatively corrosive material can preferably be used.

Throughout the description, the total of the proportion(s) of any component(s) existing in the same mixture system (such as the liquid phase in the carbonylation reactor or the liquid catalyst mixture) is not more than 100% by weight; and the proportions of the all components is 100% by weight in total.

Effects of the Invention

According to the process of the present invention, acetic acid can be produced while efficiently inhibiting (or preventing) an increase in a concentration of hydrogen iodide in the carbonylation reactor (or in the reaction mixture) or corrosion of the carbonylation reactor. In particular, according to the process, the production of acetic acid does not decline, and the production of hydrogen iodide in the carbonylation reactor or the corrosion of the carbonylation reactor can be prevented while maintaining highly efficient production. Moreover, according to the process of the present invention, the production of hydrogen iodide in the carbonylation reactor or the corrosion of the carbonylation reactor can be prevented while promoting energy-saving. Further, according to the process of the present invention, as described above, in connection with the prevention of the production of hydrogen iodide, the corrosion of the carbonylation reactor or succeeding process(es) or apparatus (e.g., a flash evaporator and a distillation column) can be prevented. Therefore, acetic acid can efficiently be produced without forming the carbonylation reactor or succeeding process(es) or apparatus with a high-quality material having a high corrosion-resistance. Thus the present invention allows use of an inexpensive or low-grade material, so that the cost of the production process of acetic acid can efficiently be reduced.

BRIEF DESCRIPTION OF DRAWINGS

FIG. 1 is a diagram for explaining a production process (or production apparatus) of acetic acid in accordance with an embodiment of the present invention.

DESCRIPTION OF EMBODIMENTS

Hereinafter, the present invention will be explained in detail with reference to the drawings. FIG. 1 is a diagram (a flow sheet, a schematic process drawing, or a schematic plant layout drawing) for explaining a production process (or production apparatus) of acetic acid in accordance with an embodiment of the present invention.

The embodiment of FIG. 1 shows a continuous process (or apparatus) for producing acetic acid ($CH_3COOH$) from a liquid reaction medium (or reaction mixture) generated by a continuous carbonylation reaction of methanol (MeOH) with carbon monoxide (CO) in the presence of a catalyst system comprising a rhodium catalyst as a metal catalyst and a co-catalyst [lithium iodide as an ionic iodide (or iodide salt) and methyl iodide], as well as acetic acid, methyl acetate, and a finite amount of water.

The process (or production apparatus) comprises a reactor (reaction system) 1 for carrying out the above-mentioned carbonylation reaction of methanol; a flasher or evaporator (flash evaporator) 2 for separating a volatile component or an acetic acid stream (a lower boiling point fraction) at least containing product acetic acid, methyl acetate, and methyl iodide, and a liquid catalyst mixture (a low-volatile component or a higher boiling point fraction) mainly containing a catalyst component (a higher boiling point component) (e.g., a rhodium catalyst and lithium iodide) from a liquid reaction medium (or a reaction mixture or a reaction solution) which is introduced from the reactor 1 through a feed line 14 and contains acetic acid generated by the reaction; a first distillation column (splitter column) 3 for separating or removing at least part of a lower boiling point fraction containing a lower boiling point component (e.g., methyl iodide, methyl acetate, and acetaldehyde) out of the volatile component introduced from the flasher 2 through a feed line 15 as an overhead from a column top thereof and withdrawing a stream containing acetic acid (an acetic acid stream) as a side stream by side cut; a second distillation column 4 for removing at least part of a lower boiling point fraction containing a lower boiling point component as an overhead from a column top thereof out of the acetic acid stream introduced from the first distillation column 3 through a feed line 23 by side cut, separating at least part of a higher boiling point component (higher boiling point impurities) (containing, e.g., water and propionic acid) from a bottom of the column, and obtaining an acetic acid stream through a feed line 29 as a side stream by side cut.

Moreover, this process is provided with a condenser or a heat exchanger for condensing a component fed through each line. Specifically, the reactor 1 is equipped with a condenser 5 for condensing a condensable component in an offgas (vapor) discharged through a discharge line 11; a recycle line 12 for recycling a liquid component condensed by the condenser 5 to the reactor 1; and a discharge line 13 for discharging a gaseous component, which is a non-condensed component in the condenser 5.

Further, in this process, the flasher 2 is equipped with a heat exchanger 6 for cooling a liquid catalyst mixture (or bottom fraction) separated by the flasher 2 and discharged from the bottom of the flasher 2 through a discharge line 18; a recycle line 19 for recycling the liquid catalyst mixture cooled by the heat exchanger 6 to the reactor 1; a heat exchanger 7 for condensing a condensable component in part of the volatile component (or volatile phase) discharged as an overhead from the flasher 2 and introduced through a feed line 15a; a discharge line 16 for discharging a gaseous component, which is a non-condensable component in the heat exchanger 7; and a recycle line 17 for recycling a liquid (or liquefied) component containing acetic acid condensed by the heat exchanger 7 to the reactor 1.

Furthermore, in this process, the first distillation column 3 is equipped with a condenser 8 for condensing a condensable component in the lower boiling point fraction or overhead discharged through a discharge line 20; a recycle line 22 for recycling a liquid component condensed by the condenser 8 to the reactor 1; a recycle line 22a for recycling (or refluxing) part of the liquid component condensed by the condenser 8 to the first distillation column 3; a discharge line 21 for discharging a gaseous component, which is a non-condensable component in the condenser 8; and a line 24 for discharging a higher boiling point fraction in the first distillation column 3 and recycling the higher boiling point fraction to the reactor 1. Incidentally, the liquid component recycled to the first distillation column 3 is used for refluxing in the first distillation column 3.

Moreover, in this process, the second distillation column 4 is equipped with a condenser 9 for condensing a condensable component in the lower boiling point fraction or overhead discharged through a discharge line 25; a recycle line 27 for recycling (or refluxing) a liquid component or lower boiling point fraction condensed by the condenser 9 to the second distillation column 4; a discharge line (recycle line) 26 for separating part or all of the liquid component or lower boiling point fraction condensed by the condenser 9 from the line 27 and recycling the separated component or fraction to the reactor 1; and a line 28 for feeding a gas separated in the condenser 9 to a scrubber 10 through a line 13.

This process shown in FIG. 1 further comprises a scrubber or scrubber system 10 for recovering the gaseous components (or non-condensed components) or others discharged from the condenser 5, the heat exchanger 7, and the condenser 8 and abandoning the components and/or recycling the components to the reaction system (e.g., the reactor 1). Incidentally, a line for recycling the gaseous component or others from the scrubber system 10 to the reaction system (e.g., the reactor 1) is omitted in FIG. 1.

Hereinafter, the process shown in FIG. 1 will be explained in more detail.

Methanol as a liquid component and carbon monoxide as a gaseous reactant may be continuously fed to the reactor 1 at a predetermined rate, and a catalyst mixture (a liquid catalyst mixture) containing a carbonylation catalyst system [a catalyst system comprising a main catalyst component (e.g., a rhodium catalyst) and a co-catalyst (e.g., lithium iodide and methyl iodide)] and water can be continuously fed to the reactor 1. Moreover, fraction(s) (e.g., in the form of liquid) containing lower boiling point fraction(s) and/or higher boiling point fraction(s) from the succeeding step(s) (e.g., the flasher 2, the first and second distillation columns 3 and 4, the heat exchanger 7, and the scrubber system 10) can also be fed to the reactor 1.

The inner pressure of the reactor 1 (e.g., reaction pressure, carbon monoxide partial pressure, hydrogen partial pressure, methane partial pressure, and nitrogen partial pressure) can be maintained by withdrawing a vapor from the column top and introducing the withdrawn vapor into the condenser 5. The withdrawn vapor is cooled by the condenser 5 to give a liquid component (containing acetic acid, methyl acetate, methyl iodide, acetaldehyde, water, and others) and a gaseous component (containing carbon monoxide, hydrogen, and others). The resulting liquid component is recycled to the reactor 1, and the resulting gaseous component (waste gas) is discharged to the scrubber system 10, and if necessary, recycled to the reactor 1. In particular, the reaction system is an exothermic reaction system that accompanies heat generation, and part of the quantity of heat generated in the reactor may be removed by cooling part of the reaction heat transferred from the reaction solution to the vapor with the condenser 5.

Since the reaction system is an exothermic reaction system that accompanies heat generation, the reactor 1 may be equipped with a heat-removable (or heat-removing) or cooling unit (e.g., a jacket) for controlling a reaction temperature. Incidentally, as described later, the process of FIG. 1 is equipped with a heat exchanger 7 for removing heat from part of a volatile component from the flash evaporator 2. Thus even when the reactor is not equipped with the heat-removable or cooling unit, the heat can be removed.

Components contained in the reaction mixture (crude reaction solution) generated in the reactor 1 may include acetic acid, hydrogen iodide, a lower boiling point component or lower boiling point impurity having a boiling point lower than that of acetic acid (e.g., methyl iodide as a co-catalyst, methyl acetate as a reaction product of acetic acid with methanol, and acetaldehyde, crotonaldehyde, 2-ethylcrotonaldehyde, and a higher iodide (such as hexyl iodide or decyl iodide) as by-products), and a higher boiling point component or higher boiling point impurity having a boiling point higher than that of acetic acid [a metal catalyst component (a rhodium catalyst, and lithium iodide as a co-catalyst), propionic acid, and water]. In the embodiment of FIG. 1, the concentration of each component in at least a composition (liquid phase) in the reactor 1 is stringently adjusted as described later, and the production (or increase in concentration) of hydrogen iodide in the reactor 1 (or reaction mixture) is significantly inhibited.

In order to mainly separate the higher boiling point component (such as the metal catalyst component) from the reaction mixture, the reaction mixture (or part of the reaction mixture) is continuously withdrawn from the reactor 1 and introduced or fed into the flasher (flash evaporator) 2. In the flasher 2, a volatile component or a lower boiling point fraction (mainly containing acetic acid which is a product and also functions as a reaction solvent, methyl acetate, methyl iodide, water, hydrogen iodide, and others) is evaporated by flash distillation to separate a liquid catalyst mixture or a higher boiling point fraction (mainly containing a metal catalyst component, e.g., a rhodium catalyst, lithium iodide, and others) from the reaction mixture. Incidentally, in the liquid catalyst mixture, the metal catalyst component, and in addition, components remaining without evaporation (e.g., acetic acid, methyl iodide, water, and methyl acetate) are also contained.

Inside of the flasher 2, the flash distillation is carried out so that at least methyl acetate in the liquid catalyst mixture may be maintained at a predetermined concentration (e.g., not less than 0.1% by weight, particularly not less than 0.6% by weight). Such conditions and the adjustment of the composition in the reactor are combined to prevent the concentration of hydrogen iodide in the flash evaporator from rising. Thus the corrosion of the evaporator can markedly be prevented. Incidentally, the concentration of methyl acetate can be adjusted by increasing the concentration of methanol in the reaction mixture and allowing the reaction of methanol with acetic acid to proceed predominantly, and others. If necessary, the concentration of methyl acetate in the flash evaporator can also be adjusted by mixing methyl acetate and/or a component producing methyl acetate (e.g., methanol and dimethyl ether) through a line 30, which joins the line 14, with the reaction mixture from the reactor 1.

The liquid catalyst mixture is continuously discharged from the bottom of the column. The discharged liquid catalyst mixture may directly be recycled to the reactor 1. In the embodiment shown in the FIGURE, the discharged liquid catalyst mixture is heat-removed (cooled) in the heat exchanger 6 and then recycled to the reactor 1.

On the other hand, the volatile component or lower boiling point fraction (acetic acid stream) is withdrawn from the column top or upper part of the flasher 2 and fed or introduced into the first distillation column 3, and part of the volatile component is introduced into the heat exchanger 7 to be condensed. The volatile component cooled by the heat exchanger 7 produces a liquid component (containing acetic acid, methanol, methyl iodide, methyl acetate, water, propionic acid, acetaldehyde, and others) and a gaseous component (containing carbon monoxide, hydrogen, and others). The resulting liquid component is recycled to the reactor 1. The resulting gaseous component (waste gas) is fed to the scrubber system 10, and if necessary, carbon monoxide is obtained without purification of the gaseous component or with purification thereof by PSA (pressure swing adsorption) method, and recycled to the reactor 1. The lower boiling point fraction is withdrawn from the flasher to introduce into the heat exchanger, and part of the reaction heat transferred from the reaction solution to the flash vapor is cooled by the heat exchanger. Accordingly, the heat can efficiently be removed. Thus, since the succeeding distillation column or condenser can be downsized (or miniaturized) even for a large-sized plant, acetic acid can be produced with a high purity and a high yield in a resource-saving and energy-saving equipment. Further, the heat can be removed without installing an external circulation cooling unit in the reactor, which leads to the prevention of carbon monoxide loss and the improvement of the reaction efficiency or the cost reduction of equipment.

In the first distillation column 3, usually, the lower boiling point fraction (or overhead) containing the lower boiling point component (containing methyl iodide, methyl acetate, acetaldehyde, water, and others) is separated from the top or upper part of the column and fed to the condenser 8, and a higher boiling point fraction containing the higher boiling point component (e.g., propionic acid, an entrained catalyst, and lithium iodide) is separated from the bottom or lower part of the column through a bottom line 24 and recycled to the reactor 1. The higher boiling point fraction (first higher boiling point fraction) contains the higher boiling point component, as well as the lower boiling point component which remains without evaporation, acetic acid, and others. Part of the higher boiling point fraction discharged through the line 24 may be recycled to the flasher 2 through a line 24a, if necessary. A side stream (acetic acid stream or crude acetic acid stream) mainly containing acetic acid is withdrawn from the first distillation column 3 by side cut and is fed or introduced into the second distillation column 4.

The lower boiling point fraction (overhead or first overhead or first lower boiling point fraction) withdrawn from the top or upper part of the first distillation column 3 contains acetic acid and others, and is fed to the condenser 8. The lower boiling point fraction withdrawn from the first distillation column 3 can be condensed by the condenser 8 to cool part of the reaction heat transferred from the reaction solution to the lower boiling point fraction through the flash vapor with the condenser 8, and thus part of the reaction heat can be removed. In the condenser 8, the lower boiling point fraction is condensed to separate a gaseous component mainly containing carbon monoxide, hydrogen and others, and a liquid component containing methyl iodide, methyl acetate, acetic acid, acetaldehyde and others. The gaseous component separated in the condenser 8 is fed to the scrubber system 10, if necessary, carbon monoxide is obtained without purification of the gaseous component or with purification thereof by PSA (pressure swing adsorption) method, and recycled to the reaction system (e.g., the reactor 1) (not shown). The liquid component separated in the condenser 8 may be recycled to the first distillation column 3 through the line 22a. Incidentally, the liquid component may be a uniform solution or a separated solution (for example, a two-phase solution) system. For example, for the liquid component containing a predetermined amount of water, the liquid component may be separated into two phases composed of an aqueous phase (aqueous layer or water phase) and an oily phase (organic layer or organic phase), where the aqueous phase contains acetic acid, acetaldehyde, and others, and the oily phase contains methyl iodide and others. Moreover, the oily phase may be recycled to the reactor 1 and/or the first distillation column 3, and the aqueous phase (water phase) may be recycled to the reactor 1 and/or the first distillation column 3.

In the acetic acid stream which is obtained by side cut from the first distillation column 3 and is fed to the second distillation column 4, a lower boiling point component (e.g., water) remaining in the acetic acid stream is further separated in the second distillation column 4, and an acetic acid stream having a higher purity (purified acetic acid stream) is withdrawn as a side stream. In the second distillation column 4, a lower boiling point fraction (overhead or second overhead or second lower boiling point fraction) containing the lower boiling point component is fed from the top or upper part of the column to the condenser 9, and a side stream (acetic acid stream) rich in acetic acid is distilled by side cut. If necessary, the lower boiling point fraction discharged from the top or upper part of the column may be recycled to the second distillation column 4 and/or the reaction system 1. Water may be separated as a lower boiling point component in the second distillation column 4, or may be mainly separated in the first distillation column 3 and further separated in the second distillation column 4 for purification. Incidentally, a higher boiling point fraction (a second higher boiling point fraction) such as a higher boiling point component (e.g., propionic acid) may be discharged from the bottom or lower part of the column, and if necessary, may be recycled to the reactor 1 or may be wasted out of the system (not shown).

The lower boiling point fraction withdrawn from the top or upper part of the second distillation column 4 contains methyl iodide, methyl acetate, water, acetaldehyde, and others, and is condensed by the condenser 9. Then the lower boiling point fraction condensed in the condenser 9 may be recycled to the reactor 1 through the line 26 or recycled to the second distillation column 4 through the line 27. Moreover, for the liquid component containing a predetermined amount of water, in the same manner as in the first distillation column, the liquid component may be separated into an aqueous phase and an oily phase, and these phases may be recycled. The lower boiling point fraction withdrawn from the second distillation column 4 is condensed by the condenser 9 to cool part of the reaction heat transferred from the reaction solution to the lower boiling point fraction through the flash vapor with the condenser 9.

[Reaction Step]

In the reaction step (carbonylation reaction step), methanol is carbonylated with carbon monoxide in the presence of the catalyst system. Incidentally, fresh methanol may be fed to the reaction system directly or indirectly, or methanol and/or a derivative thereof withdrawn from various distillation steps may be recycled and fed to the reaction system.

Inside the carbonylation reactor, a liquid-phase reaction system containing the reactant and the higher boiling point component [for example, the metal catalyst component (e.g., a rhodium catalyst) and the ionic iodide (e.g., lithium iodide)] is in equilibrium with a vapor-phase system comprising carbon monoxide, by-products by the reaction (hydrogen, methane, carbon dioxide), and a vaporized lower boiling point component (e.g., methyl iodide, acetic acid as a product, and methyl acetate), and a carbonylation reaction of methanol proceeds under stirring by a stirrer or other means.

The catalyst system may usually comprise a metal catalyst, a co-catalyst, and an accelerator. Examples of the metal catalyst may include a transition metal catalyst, in particular, a metal catalyst containing the group 8 metal of the Periodic Table (e.g., a cobalt catalyst, a rhodium catalyst, and an iridium catalyst). The catalyst may be a metal as a simple substance or may be used in the form of an oxide (including a complex metal oxide), a hydroxide, a halide (e.g., a chloride, a bromide, and an iodide), a carboxylate (e.g., an acetate), a salt of an inorganic acid (e.g., a sulfate, a nitrate, and a phosphate), a complex, and others. These metal catalysts may be used alone or in combination. The preferred metal catalyst includes a rhodium catalyst and an iridium catalyst (particularly, a rhodium catalyst).

Moreover, it is preferred to use the metal catalyst in the form dissolvable in a reaction solution. Incidentally, since rhodium usually exists as a complex in the reaction solution, the form of the rhodium catalyst is not particularly limited to a specific one as long as the catalyst can change into a complex in the reaction solution, and may be used in various forms. As such a rhodium catalyst, a rhodium iodide complex [for example, $RhI_3$, $[RhI_2(CO)_4]^-$, and $[Rh(CO)_2I_2]^-$], a rhodium carbonyl complex, or the like is particularly preferred. Moreover, the catalyst may be stabilized in the reaction solution by addition of a halide salt (e.g., an iodide salt) and/or water.

As the co-catalyst or the accelerator contained in the catalyst system, an ionic iodide (an iodide salt) is used. The iodide salt is added in order to stabilize the rhodium catalyst and inhibit side reactions, particularly, in a low water content. The iodide salt is not particularly limited to a specific one as far as the iodide salt produces an iodine ion in the reaction solution. The iodide salt may include, for example, a metal halide [for example, a metal iodide such as an alkali metal iodide (e.g., lithium iodide, sodium iodide, potassium iodide, rubidium iodide, and cesium iodide), an alkaline earth metal iodide (e.g., beryllium iodide, magnesium iodide, and calcium iodide), or an iodide of the group 3B metal of the Periodic Table (e.g., boron iodide and aluminum iodide)], an organic halide [for example, an organic iodide such as a phosphonium salt of an iodide (a phosphonium iodide) (e.g., a salt with tributylphosphine and triphenylphosphine) or an ammonium salt of an iodide (an ammonium iodide) (e.g., a salt of tertiary amine, a pyridine compound, an imidazole compound, an imide compound, or the like with an iodide), a bromide corresponding to the iodide, and a chloride corresponding to the iodide]. Incidentally, the alkali metal iodide (e.g., lithium iodide) also functions as a stabilizer for the carbonylation catalyst (e.g., a rhodium catalyst). These iodide salts may be used alone or in combination. Among these iodide salts, an alkali metal iodide (such as lithium iodide) is preferred.

As the accelerator contained in the catalyst system, an alkyl iodide (e.g., a $C_{1-4}$ alkyl iodide such as methyl iodide, ethyl iodide, or propyl iodide), particularly methyl iodide, is utilized. Thus the accelerator may contain at least methyl iodide.

In the carbonylation reaction, acetic acid is produced, and the esterification of product acetic acid with methanol is accompanied by generation of methyl acetate, water, and others. Acetic acid can also be used as a reaction solvent. Moreover, since the reaction is a consecutive reaction, such a component always exists in the carbonylation reactor. Further, such a component also exists as a component recycled from the succeeding steps.

Thus inside the carbonylation reactor, there are various components such as the produced components and the recycled components in addition to the catalyst components. According to the present invention, the production of hydrogen iodide or the corrosion of the carbonylation reactor is inhibited by adjusting (or regulating) the concentrations of these components. Hereinafter, for each of the first process and the second process, the concentration of each component will be explained separately in detail.

(First Process)

It is sufficient that the concentration of the metal catalyst (for example, the concentration of the rhodium catalyst) in the whole liquid phase in the reactor is not less than 860 ppm (e.g., 860 to 5000 ppm) on the basis of weight. For example, the concentration of the metal catalyst may be about 870 to 4000 ppm, preferably about 880 to 3000 ppm, and more preferably about 900 to 1500 ppm.

Moreover, it is sufficient that the concentration of water in the whole liquid phase in the reactor is not less than 0.8% by weight (e.g., 0.8 to 20% by weight). For example, the concentration of water may be about 0.8 to 15% by weight, preferably about 1 to 10% by weight (e.g., about 1.5 to 9% by weight), more preferably about 1.7 to 8% by weight (e.g., about 1.8 to 7% by weight), and usually about 1 to 6% by weight (e.g., about 1.5 to 5% by weight).

Further, it is sufficient that the concentration of methyl iodide in the whole liquid phase in the reactor is not more than 13.9% by weight (e.g., 1 to 13.9% by weight). For example, the concentration of methyl iodide may be about 2 to 13.9% by weight (e.g., about 3 to 13.5% by weight), preferably about 4 to 13% by weight (e.g., about 5 to 12% by weight), more preferably about 6 to 11% by weight, and usually about 4 to 13.5% by weight (e.g., about 6 to 13% by weight).

Incidentally, the concentration of the ionic iodide (e.g., lithium iodide) is not particularly limited to a specific one. For example, the concentration of the ionic iodide in the whole liquid phase in the reactor may be not more than 30% by weight (e.g., about 0.3 to 30% by weight), preferably not more than 25% by weight (e.g., about 0.5 to 25% by weight), and more preferably not more than 20% by weight (e.g., about 2 to 20% by weight).

Moreover, the concentration of methyl acetate is not particularly limited to a specific one, and the concentration of methyl acetate in the whole liquid phase in the reactor may be selected from the range of not less than 0.1% by weight (e.g., 0.2 to 25% by weight). For example, the concentration of methyl acetate may be not less than 0.3% by weight (e.g., about 0.4 to 20% by weight), preferably not less than 0.5% by weight (e.g., about 0.6 to 18% by weight), more preferably not less than 1% by weight (e.g., about 1.2 to 15% by weight), and particularly not less than 1.5% by weight (e.g., about 1.8 to 10% by weight).

Incidentally, the concentration of acetic acid in the whole liquid phase in the reactor may for example be not less than 30% by weight (e.g., about 30 to 90% by weight), preferably not less than 35% by weight (e.g., about 35 to 85% by weight), and more preferably not less than 40% by weight (e.g., about 45 to 80% by weight).

The reaction under such conditions achieves both further reduced corrosion of the reactor and further improved production of acetic acid.

(Second Process)

It is sufficient that the concentration of the metal catalyst (for example, the concentration of the rhodium catalyst) in the whole liquid phase in the reactor is not less than 660 ppm (e.g., 660 to 5000 ppm) on the basis of weight. For example, the concentration of the metal catalyst may be about 700 to 3000 ppm, preferably about 750 to 2000 ppm, and more preferably about 800 to 1500 ppm.

It is sufficient that the concentration of water in the whole liquid phase in the reactor is 0.8 to 3.9% by weight. For example, the concentration of water may be about 1 to 3.5% by weight (e.g., about 1.2 to 3.3% by weight), preferably about 1.5 to 3% by weight (e.g., about 1.7 to 2.9% by weight), and more preferably about 1.8 to 2.8% by weight.

Moreover, it is sufficient that the concentration of the ionic iodide (e.g., lithium iodide) is not more than 13% by weight. For example, the concentration of the ionic iodide may be about 0.5 to 13% by weight, preferably about 1 to 12% by weight, and more preferably about 2 to 11% by weight.

Further, it is sufficient that the concentration of methyl iodide in the whole liquid phase in the reactor is not more than 13.9% by weight (e.g., 1 to 13.9% by weight). For example, the concentration of methyl iodide may be about 2 to 13.5% by weight (e.g., about 3 to 13.5% by weight), preferably about 4 to 13% by weight (e.g., about 5 to 12% by weight), more preferably about 6 to 11% by weight, and usually about 2 to 13.9% by weight.

Moreover, the concentration of methyl acetate is not particularly limited to a specific one, and the concentration of methyl acetate in the whole liquid phase in the reactor may be selected from the range of not less than 0.1% by weight (e.g., 0.3 to 25% by weight). For example, the concentration of methyl acetate may be not less than 0.3% by weight (e.g., about 0.4 to 20% by weight), preferably not less than 0.5% by weight (e.g., about 0.6 to 18% by weight), more preferably not less than 1% by weight (e.g., about 1.2 to 15% by weight), and particularly not less than 1.5% by weight (e.g., about 1.8 to 10% by weight).

Incidentally, the concentration of acetic acid in the whole liquid phase in the reactor may for example be not less than 30% by weight (e.g., about 30 to 90% by weight), preferably not less than 35% by weight (e.g., about 35 to 85% by weight), and more preferably not less than 40% by weight (e.g., about 45 to 80% by weight).

The reaction under such conditions achieves both further reduced corrosion of the reactor and further improved production of acetic acid.

In the first and second processes, the concentration of each component can be regulated by suitably adjusting the quantity of each component to be fed to the reaction system or the quantity of each component to be recycled to the reaction system, the reaction temperature, the reaction pressure, and others; further energy-saving can be made.

The carbon monoxide to be fed to the reaction system may be used as a pure gas or may be used as a gas diluted with an inactive gas (e.g., nitrogen, helium, and carbon dioxide). Moreover, exhausted gas component(s) containing carbon monoxide obtained from the succeeding step(s) may be recycled to the reaction system. Moreover, in the carbonylation reaction, hydrogen is formed (or generated) by a shift reaction between carbon monoxide and water. In order to increase the catalyst activity, if necessary, hydrogen may be fed to the reaction system. The hydrogen may be fed as a mixed gas with carbon monoxide as a raw material to the reaction system. Moreover, the hydrogen may be fed to the reaction system by recycling gaseous component(s) (including hydrogen, carbon monoxide, and others) exhausted in the succeeding distillation step(s) (distillation column), if necessary after suitably purifying the gaseous component(s).

The carbon monoxide pressure (partial pressure) in the reactor may for example be not less than 300 kPa (e.g., about 500 to 5000 kPa), preferably not less than 600 kPa (e.g., about 800 to 4000 kPa), and more preferably not less than 900 kPa (e.g., about 1000 to 3000 kPa).

Moreover, the hydrogen partial pressure in the reactor may for example be not less than 1 kPa (e.g., about 2 to 200 kPa), preferably not less than 2 kPa (e.g., about 3 to 150 kPa), and more preferably not less than 4 kPa (e.g., about 5 to 100 kPa). By carrying out the reaction while maintaining such a carbon monoxide or hydrogen partial pressure, the production of hydrogen iodide can be inhibited while further efficiently ensuring the production efficiency of acetic acid.

The carbon monoxide partial pressure or hydrogen partial pressure in the reaction system may be adjusted, for example, by suitably adjusting the amount of the carbon monoxide and hydrogen fed and/or recycled to the reaction system, the amount of raw substances (e.g., methanol) fed to the reaction system, the reaction temperature, the reaction pressure, and others.

In the carbonylation reaction, the reaction temperature may be, for example, about 150 to 250° C., preferably about 160 to 230° C., and more preferably about 180 to 220° C. Moreover, the reaction pressure (total reactor pressure) may be, for example, about 15 to 40 atmospheres.

In the reaction system, generation of aldehydes may be depressed or inhibited by removing the aldehyde in the recycling stream from the succeeding step(s) (e.g., distillation column), or by modifying the reaction conditions, for example, reducing the proportion of the co-catalyst such as an alkyl iodide and/or the hydrogen partial pressure. Moreover, the generation of hydrogen in the reaction system may be depressed or inhibited by adjusting the concentration of water and/or the concentration of methyl acetate.

The present invention achieves not only inhibited production of hydrogen iodide but also highly efficient production of acetic acid. For example, in the first process, the production rate (reaction rate, space time yield) of acetic acid may be selected from the range of not less than 10 mol/L·h (hour) (e.g., 10 to 45 mol/L·h), and may for example be not less than 12 mol/L·h (e.g., about 12 to 35 mol/L·h) and particularly not less than 19 mol/L·h (e.g., about 19 to 35 mol/L·h, preferably about 20 to 33 mol/L·h, and more preferably about 22 to 30 mol/L·h).

In the second process, the production rate of acetic acid may be selected from the range of not less than 5 mol/L·h (e.g., 5 to 45 mol/L·h), and may for example be not less than 7 mol/L·h (e.g., about 7 to 35 mol/L·h) and preferably not less than 9 mol/L·h (e.g., about 10 to 30 mol/L·h).

The concentration of hydrogen iodide in the whole liquid phase in the reactor (or the reaction mixture) may for example be regulated (or adjusted) to not more than 1% by weight (e.g., about 0 or detection limit to 0.8% by weight), preferably not more than 0.6% by weight (e.g., about 0.001 to 0.5% by weight), more preferably not more than 0.3% by weight (e.g., about 0.01 to 0.2% by weight), and usually not more than 0.1% by weight (e.g., about 0 or detection limit to 0.09% by weight, preferably about 0 or detection limit to 0.07% by weight, and more preferably about 0 or detection limit to 0.05% by weight).

The concentration of hydrogen iodide may be measured directly or measured (or calculated) indirectly. For example, the concentration of the iodide ion derived from the iodide salt [for example, an iodide derived from the co-catalyst such as LiI, and a metal iodide (e.g., an iodide of a corroded metal (such as Fe, Ni, Cr, Mo, or Zn) produced in the process of the acetic acid production)] may be subtracted from the total concentration of iodide ions ($I^-$) to determine (or calculate) the concentration of hydrogen iodide.

The vapor component withdrawn from the top of the reactor for the purpose of the pressure control of the reactor or others is preferably cooled with a condenser, a heat exchanger or other means to remove part of the reaction heat. It is preferable that the cooled vapor component be separated into a liquid component (containing acetic acid, methyl acetate, methyl iodide, acetaldehyde, water, and others) and a gaseous component (containing carbon monoxide, hydrogen, and others), the liquid component be recycled to the reactor and the gaseous component be introduced into the scrubber system.

The material of (or for forming) the carbonylation reactor is not particularly limited to a specific one and may be a metal, a ceramic, a glass, or others. Practically, a carbonylation reactor made of a metal is used. In particular, according to the present invention, in connection with the significant prevention of the concentration of hydrogen iodide in the inside of the reactor from rising, and others, the corrosion of the carbonylation reactor can be inhibited. Thus, as a carbonylation reactor (reaction vessel) in the present invention, there may be used not only a reactor made of an expensive material having a high corrosion resistance (such as zirconium) but also a reactor made of a relatively inexpensive material having not a very high corrosion resistance, for example, a metal as a simple substance (such as titanium or aluminum) and an alloy [for example, a transition-metal-based alloy such as an iron-based alloy (or an alloy containing iron as a main component, e.g., a stainless steel (including a stainless steel containing chromium, nickel, molybdenum and others)), a nickel-based alloy (or an alloy containing nickel as a main component, e.g., HASTELLOY (brand name) and INCONEL (brand name)), a cobalt-based alloy (or an alloy containing cobalt as a main component), or a titanium alloy; and an aluminum alloy].

The reaction system (or the reaction mixture) also contains methanol (unreacted methanol). Such methanol may be adjusted in association with the concentration of methyl acetate, as described later. The concentration of methanol in the reaction system may for example be not more than 1% by weight (e.g., about 0 to 0.8% by weight), preferably not more than 0.5% by weight (e.g., about 0 to 0.3% by weight), more preferably not more than 0.3% by weight (e.g., about 0 to 0.2% by weight), and usually not more than the detection limit (e.g., 0.1% by weight).

[Flash Distillation Step or Catalyst Separation Step]

In the flash distillation step (flasher), from the reaction mixture fed from the reaction step or the reactor to the flasher (flash evaporator or flash distillation column), a low-volatile component or liquid catalyst mixture (a higher boiling point fraction) containing at least a higher boiling point catalyst component (a metal catalyst component, e.g., a rhodium catalyst and an ionic iodide salt) is separated as a liquid (component), and a volatile component or volatile phase (a lower boiling point fraction) containing acetic acid is separated as a vapor (component).

In the flash distillation step (flash evaporation step), the reaction mixture may be separated into the vapor component (or vaporized stream) and the liquid component (or liquid stream) with or without heating. For example, in adiabatic flash, the reaction mixture may be separated into the vapor component and the liquid component without heating and with reduced pressure, and in thermostatic flash, the reaction mixture may be separated into the vapor component and the liquid component with heating (and reduced pressure). The reaction mixture may be separated into the vapor component and the liquid component by combining these flash conditions.

In the flash distillation, the distillation temperature (or the reaction temperature) may for example be about 100 to 260° C. (e.g., about 110 to 250° C.), preferably about 120 to 240° C. (e.g., about 140 to 230° C.), more preferably about 150 to 220° C. (e.g., about 160 to 210° C.), and particularly about 170 to 200° C. Moreover, in the flash distillation, the temperature of the liquid catalyst mixture (or the liquid temperature of the reaction mixture) may for example be about 80 to 200° C. (e.g., about 90 to 180° C.), preferably about 100 to 170° C. (e.g., about 120 to 160° C.), and more preferably about 130 to 160° C. Further, in the flash distillation, the absolute pressure may be about 0.03 to 1 MPa (e.g., about 0.05 to 1 MPa), preferably about 0.07 to 0.7 MPa, and more preferably about 0.1 to 0.5 MPa (e.g., about 0.15 to 0.4 MPa). Hydrogen iodide is easily produced (or the concentration of hydrogen iodide tends to increase) under such a relatively high temperature (and high pressure) condition. According to the present invention, however, even under such a condition, since the production of hydrogen iodide in the carbonylation reaction is inhibited, the production or increased concentration of hydrogen iodide in the flash evaporator can efficiently be inhibited.

The inner temperature and/or pressure in the flasher may be lowered compared with those in the reactor so that further production of by-products or lowering of the catalyst activity may be inhibited.

The separation (flash distillation) of the metal catalyst component may usually be carried out with the use of a distillation column (a flash evaporator). Moreover, the metal catalyst component may be separated by means of flash distillation in combination with a mist-collecting method or a solid-collecting method which is widely used in industrial application.

The material of (or forming) the flasher is not particularly limited to a specific one and may include the same material as that of the carbonylation reactor. According to the present invention, due to the significant prevention of the concentration of hydrogen iodide in the inside of the flash evaporator from rising, the corrosion of the flash evaporator can also be inhibited at a high level. Therefore, according to the present invention, as the flash evaporator, there may also be used a flash evaporator made of the same material, which is relatively inexpensive material having not a very high corrosion resistance, as that of the carbonylation reactor.

The separation step of the liquid catalyst mixture may be composed of a single step, or may be composed of a plurality of steps in combination. The liquid catalyst mixture or higher boiling point catalyst component (metal catalyst component) separated by such step(s) may usually be recycled to the reaction system, as shown in the embodiment of the FIGURE. Moreover, the liquid catalyst mixture may be cooled (or heat-removed) by the heat exchanger and recycled to the reactor, as shown in the example of the FIGURE. The cooling can improve the heat removal efficiency of the whole system.

The separated liquid catalyst mixture (or low-volatile component or higher boiling point fraction) contains the metal catalyst (e.g., a rhodium catalyst), the ionic iodide (e.g., an alkali metal iodide such as lithium iodide), and in addition, components remaining without evaporation (e.g., acetic acid, methyl iodide, water, methyl acetate, and hydrogen iodide).

In the flash distillation (or flash evaporator), the ratio (weight ratio) of the volatile component to be separated relative to the liquid catalyst mixture (or low-volatile component) may be about 10/90 to 50/50, preferably about 15/85 to 40/60, and more preferably about 20/80 to 35/65 in a ratio of the former/the latter.

According to the present invention, among the components in the liquid catalyst mixture, the concentration of at least methyl acetate may be adjusted (or regulated). According to the present invention, the adjustment of the concentration and the inhibitory action against the production of hydrogen iodide in the carbonylation reaction are combined, so that the production or increased concentration of hydrogen iodide in the flash evaporator can further efficiently be inhibited in a wide range of flash reaction conditions. Multiple factors are involved in the reason why the increase in concentration of hydrogen iodide is prevented by adjusting the concentration of methyl acetate, and one of the factors includes consumption of hydrogen iodide by the following equilibrium reaction. Incidentally, the same equilibrium reaction also applies to hydrogen iodide in the reaction mixture.

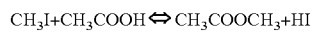

The concentration of methyl acetate in the liquid catalyst mixture may be selected from the range of not less than 0.05% by weight (e.g., 0.1 to 20% by weight), and may for example be not less than 0.2% by weight (e.g., about 0.3 to 15% by weight), preferably not less than 0.5% by weight (e.g., about 0.6 to 10% by weight), and usually about 0.8 to 5% by weight (e.g., 1 to 4% by weight). In particular, the concentration of methyl acetate in the liquid catalyst mixture may be not less than 0.6% by weight (e.g., about 0.6 to 20% by weight), preferably not less than 0.7% by weight (e.g., about 0.7 to 15% by weight), more preferably not less than 0.8% by weight (e.g., about 0.8 to 10% by weight), and usually about 0.7 to 5% by weight (e.g., about 0.7 to 3% by weight, preferably about 0.8 to 2% by weight, and more preferably about 0.9 to 1.5% by weight). The concentration of methyl acetate is adjusted to the range, so that the production or increased concentration of hydrogen iodide can further efficiently be inhibited.

The concentration of water in the liquid catalyst mixture may for example be selected from the range of not more than 15% by weight (e.g., 0.1 to 12% by weight), and may for example be not more than 10% by weight (e.g., about 0.5 to 10% by weight), preferably not more than 8% by weight (e.g., about 0.8 to 8% by weight), and more preferably not more than 5% by weight (e.g., about 1 to 4% by weight).

Moreover, the concentration of acetic acid in the liquid catalyst mixture may for example be not less than 30% by weight (e.g., about 35 to 95% by weight), preferably not less than 40% by weight (e.g., about 45 to 90% by weight), and more preferably not less than 50% by weight (e.g., about 50 to 85% by weight) and may usually be about 60 to 90% by weight (e.g., about 70 to 90% by weight, and preferably about 75 to 85% by weight).

Further, the concentration of methyl iodide in the liquid catalyst mixture may be selected from the range of not more than 10% by weight (e.g., 0.001 to 8% by weight), and may for example be not more than 7% by weight (e.g., about 0.005 to 6% by weight), preferably not more than 5% by weight (e.g., about 0.01 to 4% by weight), more preferably not more than 3% by weight (e.g., about 0.05 to 2.5% by weight), particularly not more than 2% by weight (e.g., about 0.1 to 1.8% by weight) and may usually be about 0.1 to 3% by weight (e.g., about 0.3 to 2.5% by weight, preferably about 0.5 to 2% by weight, and more preferably about 1 to 1.5% by weight).

Furthermore, the concentration of the ionic iodide in the liquid catalyst mixture may for example be not more than 60% by weight (e.g., about 1 to 55% by weight), preferably not more than 50% by weight (e.g., about 2 to 45% by weight), more preferably not more than 40% by weight (e.g., about 3 to 37% by weight), and particularly not more than 36% by weight (e.g., about 5 to 35% by weight). Multiple factors are also involved in the reason why the increase in concentration of hydrogen iodide is prevented by adjusting the concentration of the ionic iodide, and one of the factors includes consumption of hydrogen iodide by the following equilibrium reaction. Incidentally, the same equilibrium reaction also applies to hydrogen iodide in the reaction mixture.

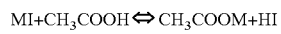

[In the formula, M represents a residue of an ionic iodide (or cationic group, e.g., an alkali metal such as lithium)]

Incidentally, the concentration of the metal catalyst in the liquid catalyst mixture may for example be not less than 700 ppm (e.g., about 750 to 10000 ppm), preferably not less than 800 ppm (e.g., about 850 to 5000 ppm), and more preferably not less than 900 ppm (e.g., about 950 to 3000 ppm) on the basis of weight.

Moreover, the concentration of methanol in the liquid catalyst mixture may for example be not more than 1% by weight (e.g., about 0 to 0.8% by weight), preferably not more than 0.5% by weight (e.g., about 0 to 0.3% by weight), and more preferably not more than 0.3% by weight (e.g., about 0 to 0.2% by weight). As described later, as the concentration of methanol is higher, the concentration of methyl acetate in the liquid catalyst mixture is easily and efficiently increased.

The adjustment of the concentrations of the constituents in the liquid catalyst mixture (increase or decrease in concentration) is not particularly limited to a specific one, and the concentrations may be adjusted by the flash distillation condition, the quantity of the process solution to be recycled from the succeeding reaction (step(s)), and others. If necessary, in order to adjust the concentration of each component, a component for increasing or decreasing the concentration of each component [for example, an ester (e.g., an acetate ester), an alcohol, and an ether] may be added to the reaction mixture and/or the flash evaporator. Such a component may be a component (a basic component) reactive to hydrogen iodide.

For example, the concentration of methyl acetate in the liquid catalyst mixture can efficiently be increased by increasing the concentration of methanol in the reaction mixture (or liquid catalyst mixture). That is, as represented by the following formula, methanol is allowed to react with acetic acid to produce methyl acetate (equilibrium reaction). Thus the production reaction of methyl acetate easily occurs as the concentration of methanol increases. As a result, the concentration of methyl acetate in the liquid catalyst mixture can be increased. Incidentally, the same equilibrium reaction also applies to hydrogen iodide in the reaction mixture.

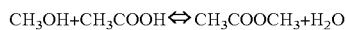

$$CH_3OH + CH_3COOH \Leftrightarrow CH_3COOCH_3 + H_2O$$

In the range that the production efficiency of acetic acid is ensured sufficiently, the concentration of methanol can be increased by increasing the concentration of methanol to be fed in the reaction or by decreasing the reaction rate to inhibit consumption of methanol. The reaction rate can be adjusted by suitably selecting the reaction temperature, the concentration of the catalyst (e.g., the concentration of methyl iodide and the concentration of the metal catalyst), the concentration of carbon monoxide (or carbon monoxide partial pressure), and others. The concentration of methanol may be adjusted by adding methanol directly, as described later.

Moreover, the concentration of methyl acetate in the liquid catalyst mixture may be adjusted by adding methyl acetate and/or a component for producing methyl acetate (e.g., methanol and dimethyl ether). Incidentally, as described above, methanol is allowed to react with acetic acid to produce methyl acetate; and dimethyl ether is allowed to react with hydrogen iodide or others to give methanol, which is allowed to react with acetic acid to produce methyl acetate. If necessary, a component for increasing or decreasing the concentration of each component may be added or mixed in the form of a mixture containing a solvent.

When the increasing or decreasing component is added to the reaction mixture, the position (or timing) of addition is not particularly limited to a specific one as far as the increasing or decreasing component is added before the reaction mixture is fed to the flash evaporator. The increasing or decreasing component may be fed to the reactor. In terms of process efficiency, the increasing or decreasing component may be fed to the reaction mixture after the reaction mixture is discharged from the reactor and before the reaction mixture is fed to the flash evaporator (for example, as shown in the FIGURE, the increasing or decreasing component may be fed to a line for feeding the flash evaporator with the reaction mixture discharged from the reactor).

Moreover, when the increasing or decreasing component is added to the flash evaporator (or the increasing or decreasing component is mixed to the reaction mixture in the flash evaporator), the position (height level) of addition is not particularly limited to a specific one. The increasing or decreasing component may be added to either the liquid phase portion or the gaseous phase portion in the flash evaporator, or both. The increasing or decreasing component may be added to the process solution to be recycled from the succeeding step(s) to the flash evaporator.

The volatile component (acetic acid stream) separated in the flasher contains product acetic acid, in addition, methyl iodide, an ester of the product acetic acid with methanol (e.g., methyl acetate), water, a very small amount of by-product(s) (e.g., acetaldehyde and propionic acid) and others. The volatile component may be distilled in the first distillation column and the second distillation column to produce purified acetic acid.

According to the present invention, the production or increased concentration of hydrogen iodide in the flasher can be inhibited. Thus the concentration of hydrogen iodide in the gaseous phase or volatile component in the inside of the flasher may for example be regulated to not more than 1% by weight (e.g., about 0 or detection limit to 8000 ppm), preferably not more than 5000 ppm (e.g., about 1 to 4000 ppm), and more preferably not more than 3000 ppm (e.g., about 10 to 2000 ppm) on the basis of weight. Moreover, the concentration of hydrogen iodide in the liquid catalyst mixture may for example be regulated to not more than 1% by weight (e.g., about 0 to 8000 ppm), preferably not more than 5000 ppm (e.g., about 1 to 4000 ppm), and more preferably not more than 3000 ppm (e.g., about 10 to 2000 ppm).

Part of the separated volatile component (acetic acid stream) may be introduced into a condenser or a heat exchanger for cooling or heat-removal, as the embodiment illustrated in the FIGURE. Since the reaction heat transferred from the reaction solution to the flash vapor can partly be cooled by the heat removal, the heat removal efficiency can be improved, and acetic acid with a high purity can be produced without installing an external circulation cooling unit in the reactor. Moreover, the cooled volatile component may be recycled to the reaction system, as the embodiment illustrated in the FIGURE. On the other hand, the gaseous component in the cooled volatile component may be introduced into the scrubber system.

[Acetic Acid Collection Step]

In the acetic acid collection step (distillation step), acetic acid is collected by separating a stream containing acetic acid from the volatile component. The separation method is not particularly limited to a specific one. Usually, the separated volatile component is fed to the distillation column (splitter column), and separated into a lower boiling point fraction (overhead) containing a lower boiling point component (e.g., methyl iodide, acetic acid, methyl acetate, and by-product acetaldehyde) and a stream containing acetic acid (acetic acid stream) by distillation. The acetic acid collection step is not necessarily the embodiment shown in the FIGURE, and may be a step in which a treatment for removing the lower boiling point component and a treatment for removing water are carried out in a single distillation column (for example, a step utilizing a distillation column described in Japanese Patent No. 3616400 publication) or a step in which a treatment for removing the lower boiling point component and a treatment for removing water in a first distillation column is followed by a further purification step in a second distillation column. Considering the purification efficiency and others, a preferably usable step includes a distillation step in which the treatment for removing the lower boiling point component is mainly carried out in the first distillation column and the treatment for removing water is mainly carried out in the second distillation column.

(First Distillation Column)

Part of the acetic acid stream (lower boiling point fraction) fed from the flasher is introduced into the heat exchanger, and the remaining (residual) acetic acid stream is fed to the first distillation column. Incidentally, the whole quantity may be fed to the first distillation column without introduction into the heat exchanger. In the first distillation column, a lower boiling point fraction (or first lower boiling point fraction or first overhead) containing at least part of an lower boiling point component (e.g., methyl iodide, methyl acetate, and acetaldehyde) and a higher boiling point fraction (or bottom fraction) containing at least part of a higher boiling point component (e.g., propionic acid and water) are separated from the acetic acid stream, and a stream containing at least acetic acid is withdrawn. In the embodiment of FIG. 1, the stream containing acetic acid is withdrawn as a side stream by side cut. The stream containing acetic acid may be withdrawn from the bottom of the column.

As described above, the acetic acid stream fed to the first distillation column is not limited to an acetic acid stream obtained by removing the rhodium catalyst component from the reaction mixture of the reaction system. The acetic acid stream may contain at least acetic acid, the lower boiling point component, the higher boiling point component, and others; or simply may be a mixture of these components.

As the first distillation column, there may be used, for example, a conventional distillation column, e.g., a distillation column such as a plate column or a packed column. The material of (or forming) the first distillation column may include the same material as that of the carbonylation reactor. According to the present invention, the production or increased concentration of hydrogen iodide in the carbonylation reaction step or the flash distillation step can be inhibited. Thus as the first distillation column, there may be used a distillation column made of the same material, which is relatively inexpensive material (e.g., an alloy), as that of the carbonylation reactor or the flash evaporator.

The distillation temperature and pressure in the first distillation column may suitably be selected depending on the condition such as the species of the distillation column, or the main subject (target) for removal selected from the lower boiling point component and the higher boiling point component. For example, for the plate column, the inner pressure of the column (usually, the pressure of the column top) may be about 0.01 to 1 MPa, preferably about 0.01 to 0.7 MPa, and more preferably about 0.05 to 0.5 MPa in terms of gauge pressure.

Moreover, in the first distillation column, the inner temperature of the column (usually, the temperature of the column top) may be adjusted by adjusting the inner pressure of the column, and may be, for example, about 20 to 180° C., preferably about 50 to 150° C., and more preferably about 100 to 140° C.

Moreover, for the plate column, the theoretical number of plates is not particularly limited to a specific one, and, depending on the species of the component to be separated, is about 5 to 50, preferably about 7 to 35, and more preferably about 8 to 30. Further, in order to separate acetaldehyde highly (or with a high precision) in the first distillation column, the theoretical number of plates may be about 10 to 80, preferably about 12 to 60, and more preferably about 15 to 40.

In the first distillation column, the reflux ratio may be selected from, for example, about 0.5 to 3,000, and preferably about 0.8 to 2,000 depending on the above-mentioned theoretical number of plates, or may be reduced by increasing the theoretical number of plates. Incidentally, in the first distillation column, the distillation may be carried out without reflux.

Since the lower boiling point fraction separated from the first distillation column contains a useful component (e.g., methyl iodide and methyl acetate), the lower boiling point fraction may directly be recycled to the reaction system (or reactor) and/or the first distillation column, or may be liquefied by heat-removing part of the reaction heat in the reaction system (e.g., the reactor) using a condenser, a heat exchanger, or other means and then recycled to the reactor and/or the first distillation column. For example, the lower boiling point fraction withdrawn from the first distillation column is not necessary recycled to the first distillation column after condensation by the condenser as the embodiment of FIG. 1. The withdrawn lower boiling point fraction may directly be recycled, or simply cooled to remove an offgas component (e.g., carbon monoxide and hydrogen) and then the remaining (residual) liquid component may be recycled. Moreover, among lower boiling point components in the lower boiling point fraction, acetaldehyde deteriorates the quality of acetic acid as a final product. Thus, if necessary, after removing acetaldehyde (e.g., after removing acetaldehyde by subjecting the fraction containing the lower boiling point impurities to the after-mentioned acetaldehyde separation step (acetaldehyde-separating column)), the remaining component(s) may be recycled to the reaction system and/or the first distillation column. Incidentally, the offgas component may be introduced into the scrubber system.

The higher boiling point fraction (bottom fraction or first higher boiling point fraction) separated in the first distillation column contains water, acetic acid, an entrained rhodium catalyst, lithium iodide, in addition, acetic acid remaining without being evaporated, the lower boiling point impurities, and others. Thus, if necessary, the higher boiling point fraction may be recycled to the reaction system (reactor) and/or the flasher. Incidentally, prior to recycling, propionic acid, which deteriorates the quality of acetic acid as a final product, may be removed off.

(Second Distillation Column)

In the second distillation column, hydrogen iodide, a lower boiling point component, and a higher boiling point component, each of which remains without being separated, in the first distillation column are removed with further high precision. As the second distillation column, there may be used a conventional distillation column, for example, a plate column, a packed column, and other columns. The material of (or forming) the second distillation column may include the same material as that of the first distillation column. According to the present invention, as described above, the production or increased concentration of hydrogen iodide in the carbonylation reaction step or the flash distillation step can be inhibited. Thus as the second distillation column, there may be used a distillation column made of the same material, which is relatively inexpensive material (e.g., an alloy), as that of the carbonylation reactor or the flash evaporator. Moreover, the inner temperature of the column, the inner pressure of the column, the theoretical number of plates, and the reflux ratio in the second distillation column may be selected depending on the species of the distillation column, for example, may be selected from the same (similar) range with the range of the above first distillation column.

Since the lower boiling point fraction (second lower boiling point fraction or second overhead) separated from the second distillation column contains a useful component such as methyl iodide or methyl acetate, the lower boiling point fraction may directly be recycled to the reaction system (e.g., the reactor) and/or the second distillation column. In order to remove part of the reaction heat, as the same manner as the lower boiling point fraction withdrawn from the first distillation column, the lower boiling point fraction may be liquefied by a condenser, a heat exchanger, or other means and then recycled. Moreover, since the lower boiling point fraction sometimes contains acetaldehyde, the lower boiling point fraction may for example be recycled after removing acetaldehyde with the after-mentioned aldehyde-separating column, if necessary. Incidentally, the offgas component may be introduced into the scrubber system.

Further, the higher boiling point fraction (second higher boiling point fraction) may be discharged from the bottom or lower part of the column. Since the higher boiling point fraction separated from the second distillation column contains propionic acid, and others, the higher boiling point fraction may directly be discarded (or removed off). Moreover, since the higher boiling point fraction further sometimes contains acetic acid, if necessary, the higher boiling point fraction from which propionic acid is removed and/or recovered may be recycled to the reaction system (e.g., the reactor).

In the second distillation column, the purified acetic acid stream is withdrawn by side cut in the embodiment of FIG. 1. The position of the side stream port may usually be at a middle or lower part of the distillation column, or the acetic acid stream may be withdrawn from the bottom of the column. Incidentally, by withdrawing the acetic acid stream from the side stream port existing at an upper position relative to the bottom port for withdrawing the higher boiling point fraction, the side stream and the higher boiling point fraction may efficiently be separated.

[Iodide Removal Step]

The purified acetic acid recovered is usually introduced into a column for product acetic acid and obtained as product acetic acid. Prior or posterior to introduction into the column for product acetic acid, the purified acetic acid may further be subjected to an iodide-removing step to remove an iodide (e.g., a $C_{1-15}$ alkyl iodide such as hexyl iodide or decyl iodide).

In the iodide removal step (or iodide-removing step), the acetic acid stream may be contacted with a remover (removing agent or material) having an iodide-removability or iodide-adsorbability (e.g., a zeolite, an activated carbon, and an ion exchange resin). In order to efficiently remove the iodide from the acetic acid stream which is continuously obtained (in a continuous system), an ion exchange resin having iodide-removability or iodide-adsorbability, particularly an iodide-removing column provided with the ion exchange resin therein is advantageously used.

The ion exchange resin to be used is usually an ion exchange resin (usually a cation exchange resin) in which at least part of the active site (e.g., usually an acidic group such as a sulfone group, a carboxyl group, a phenolic hydroxyl group, or a phosphone group) is substituted or exchanged with a metal. The metal may include, for example, at least one member selected from the group consisting of silver (Ag), mercury (Hg), and cupper (Cu). The cation exchange resin as a base (substrate) may be any one of a strong acidic cation exchange resin and a weak (mild) acidic cation exchange resin, and the preferred one includes a strong acidic cation exchange resin, for example, a macroreticular ion exchange resin, and the like.

In the ion exchange resin, the proportion of the active site exchanged to the metal (or substituted with the metal) may be, for example, about 10 to 80% by mol, preferably about 25 to 75% by mol, and more preferably about 30 to 70% by mol.

At least contacting of the acetic acid stream from the second distillation column with the ion exchange resin (preferably passing of the acetic acid stream through the ion exchange resin) achieves removal of the iodide. While contacting with (or passing through) the ion exchange resin, if necessary, the temperature of the acetic acid stream may be increased (or elevated) stepwise. The stepwise temperature elevation ensures to inhibit outflow or effusion of the metal from the ion exchange resin, as well as to remove the iodide efficiently.

Examples of the iodide-removing column may include a packed column packing inside thereof at least the ion exchange resin which is exchanged with a metal, a column provided with a bed of an ion exchange resin (e.g., a bed comprising a particulate resin) (a guard bed) and the like. The iodide-removing column may be provided with the metal-exchanged ion exchange resin, and in addition, another ion exchange resin (e.g., a cation exchange resin, an anion exchange resin, and a nonion exchange resin) inside thereof. Even when the metal is effused from the metal-exchanged ion exchange resin, arrangement of the cation exchange resin at the downstream side of the metal-exchanged ion exchange resin (e.g., arrangement of the cation exchange resin by packing, or arrangement of the cation exchange resin as a resin bed) allows the effused metal to be captured with the cation exchange resin and be removed from the carboxylic acid stream.

The temperature of the iodide-removing column may be, for example, about 18 to 100° C., preferably about 30 to 70° C., and more preferably about 40 to 60° C.

The rate of the acetic acid stream to be passed through is not limited to a specific one, and may be, for example, in an iodide-removing column utilizing a guard bed, e.g., about 3 to 15 BV/h (bed volume per hour), preferably about 5 to 12 BV/h, and more preferably about 6 to 10 BV/h.

In the iodide-removing step, the acetic acid stream may be at least contacted with the metal-exchanged ion exchange resin. For example, the iodide-removing column may comprise a column provided with the metal-exchanged ion exchange resin and a column provided with another ion exchange resin. For example, the iodide-removing column may comprise an anion exchange resin column, and a metal-exchanged ion exchange resin column on the downstream side of the anion exchange resin column, or may comprise a metal-exchanged ion exchange resin column, and a cation exchange resin column on the downstream side of the metal-exchanged ion exchange resin column. The details of the former example can be referred by WO02/062740, and others.

[Acetaldehyde Separation Step]

When the fraction containing acetaldehyde generated by the reaction is recycled and circulated to the reaction system, the amount of by-product(s) such as propionic acid, an unsaturated aldehyde, or an alkyl iodide increases. Thus, it is preferred to remove acetaldehyde in the solution to be recycled. In particular, removal of acetaldehyde is preferred, because it is unnecessary to separate and remove propionic acid, which makes acetic acid sub-standard, in the second distillation column. The method for separating acetaldehyde may comprise feeding a recycle solution (a solution to be recycled) to the acetaldehyde-separating column to separate a lower boiling point fraction containing acetaldehyde and a higher boiling point fraction containing methyl iodide, methyl acetate, water, and others, and then separating acetaldehyde from the top or upper part of the aldehyde-separating column, with the offgas component (e.g., carbon monoxide and hydrogen). Further, the offgas component may be previously removed off with a condenser or a cooling unit, prior to the separation of acetaldehyde. Furthermore, since the higher boiling point fraction obtained by removing acetaldehyde as the lower boiling point fraction contains methyl iodide, water, methyl acetate, acetic acid, and the like, the higher boiling point fraction may be recycled to the reaction system.

As the aldehyde-separating column, for example, there may be used a conventional distillation column, e.g., a plate column, a packed column, a flash evaporator, and others.

The temperature (the temperature of the column top) and the pressure (the pressure of the column top)) in the acetaldehyde-separating column may be selected depending on the species of the distillation column and others, and is not particularly limited to a specific one as far as at least acetaldehyde is separable as a lower boiling point fraction from the recycle solution [for example, the lower boiling point fraction (s) obtained in the first and/or second distillation column(s)] by utilizing difference between acetaldehyde and other components (particularly methyl iodide) in boiling point. For example, for the plate column, the pressure may be about 0.01 to 1 MPa, preferably about 0.01 to 0.7 MPa, and more preferably about 0.05 to 0.5 MPa as a gauge pressure. The inner temperature of the column is, for example, about 10 to 150° C., preferably about 20 to 130° C., and more preferably about 40 to 120° C. The theoretical number of plates may be, for example, about 5 to 150, preferably about 8 to 120, and more preferably about 10 to 100.

In the acetaldehyde-separating column, the reflux ratio may be selected from about 1 to 1000, preferably about 10 to 800, and preferably about 50 to 600 (e.g., about 70 to 400) depending on the above-mentioned theoretical number of plates.

EXAMPLES

The following examples are intended to describe this invention in further detail and should by no means be interpreted as defining the scope of the invention.

Comparative Examples 1 to 8 and Examples 1 to 9

As shown in FIG. 1, acetic acid production process was carried out continuously. The detail of the process will be described below.

CO and methanol were fed to the reactor 1, the process was started at a reaction temperature of 185° C. and a reaction pressure of 2.8 MPa, and each composition of methyl iodide, water, methyl acetate, acetic acid, lithium iodide, and rhodium was adjusted to those shown in Table 1 (the methanol content was not more than the detection limit). Thereafter, test pieces of various materials shown in Table 1 were added to the reactor 1. After leaving for 100 hours, each test piece was examined for a corrosion test.

The corrosion test was evaluated on the basis of the following criteria in Comparative Examples 1 to 4 and Examples 1 to 3 and evaluated on the observed corrosion amount in Comparative Examples 5 to 8 and Example 4 to 9.
"A": Test piece is not corroded at all.
"B": Test piece is hardly corroded.
"C": Test piece is slightly corroded.
"D": Test piece is significantly corroded.

The detail of the liquid composition and the results are shown in Tables 1 and 2. In Tables 1 and 2, "ppm" represents a concentration of Rh (rhodium) on the basis of weight, "wt %" means % by weight, "STY" represents a production rate of acetic acid, "Ac" represents acetic acid, "MA" represents methyl acetate, "MeOH" represents methanol, "MeI" represents methyl iodide, "Zr" represents zirconium, "HB2" represents a nickel-based alloy (HASTELLOY B2 manufactured by Oda Koki Co., Ltd.), "HC" represents a nickel-based alloy (HASTELLOY C manufactured by Oda Koki Co., Ltd.), the unit "mol/L·h" means the molar quantity (mol) of acetic acid produced in 1 L of the reaction solution per hour, and the unit "mm/Y" means the corrosion rate of the test piece per year (the decreased thickness (mm) of the test piece per year). Moreover, in Table 2, "-" means that the corrosion amount could not be measured due to significant corrosion. As the Rh catalyst, $RhI_3$ was used. The concentration of the iodide ion derived from the iodide salt was subtracted from the total concentration of iodide ions ($I^-$) to calculate the concentration of hydrogen iodide.

TABLE 1

| | Compositions and conditions of corrosion test | | | | | | | | | | | |
|---|---|---|---|---|---|---|---|---|---|---|---|---|
| | Ac | MA | MeOH | HI | MeI | $H_2O$ | Rh | LiI | STY | Corrosion test results | | |
| | wt % | wt % | wt % | wt % | wt % | wt % | ppm | wt % | mol/L · h | Zr | HB2 | HC |
| Comparative Example 1 | 78.3 | 0.6 | less than 0.1 | 0.4 | 10 | 0.5 | 500 | 10 | 4.0 | A | C | D |
| Comparative Example 2 | 58.7 | 0.6 | less than 0.1 | 0.5 | 10 | 20 | 470 | 10 | 7.5 | A | C | D |
| Comparative Example 3 | 63.6 | 0.6 | less than 0.1 | 0.6 | 15 | 10 | 510 | 10 | 9.2 | A | C | D |
| Comparative Example 4 | 68.6 | 0.01 | less than 0.1 | 1.2 | 10 | 10 | 490 | 10 | 3.0 | A | C | D |
| Example 1 | 76.6 | 0.6 | less than 0.1 | 0.4 | 10 | 2 | 890 | 10 | 7.1 | A | B | C |
| Example 2 | 75.0 | 0.6 | less than 0.1 | 0.4 | 10 | 3.5 | 1000 | 10 | 10.1 | A | B | C |
| Example 3 | 68.1 | 4 | less than 0.1 | 0.1 | 12 | 3.5 | 1000 | 12 | 20.3 | A | B | C |

TABLE 2

| | Compositions and conditions of corrosion test | | | | | | | | | Corrosion test results | | |
|---|---|---|---|---|---|---|---|---|---|---|---|---|
| | Ac wt % | MA wt % | MeOH wt % | HI wt % | MeI wt % | H₂O wt % | Rh ppm | LiI wt % | STY mol/L·h | Zr mm/Y | HB2 mm/Y | HC mm/Y |
| Comparative Example 5 | 58.4 | 0.7 | less than 0.1 | 0.4 | 10.5 | 20 | 470 | 9.8 | 7.9 | less than 0.03 | 0.25 | — |
| Comparative Example 6 | 62.8 | 0.6 | less than 0.1 | 0.5 | 15.1 | 10 | 510 | 10.8 | 9.4 | less than 0.03 | 0.2 | — |
| Comparative Example 7 | 68.2 | 0.01 | less than 0.1 | 1.3 | 10.1 | 10 | 490 | 10.2 | 3.1 | less than 0.03 | 0.3 | — |
| Comparative Example 8 | 68.4 | 0.08 | less than 0.1 | 1.0 | 10.1 | 10 | 490 | 10.2 | 3.1 | less than 0.03 | 0.4 | — |
| Example 4 | 76.2 | 0.7 | less than 0.1 | 0.3 | 10.5 | 2 | 890 | 9.9 | 10.0 | less than 0.03 | 0.06 | 1.2 |
| Example 5 | 74.4 | 0.6 | less than 0.1 | 0.3 | 10 | 3.5 | 1010 | 10.7 | 10.9 | less than 0.03 | 0.08 | 1.4 |
| Example 6 | 72.9 | 0.6 | less than 0.1 | 0.3 | 12.2 | 3.5 | 1005 | 10.2 | 12.4 | less than 0.03 | 0.09 | 1.5 |
| Example 7 | 70.3 | 3.9 | less than 0.1 | 0.1 | 11.9 | 3.5 | 998 | 10 | 17.8 | less than 0.03 | 0.07 | 1.3 |
| Example 8 | 69.0 | 4.1 | less than 0.1 | 0.1 | 12.4 | 1.8 | 1200 | 12.3 | 20.3 | less than 0.03 | 0.05 | 0.9 |
| Example 9 | 73.3 | 1.8 | less than 0.1 | 0.3 | 12 | 1.2 | 1020 | 11 | 10.5 | less than 0.03 | 0.05 | 1.0 |

As apparent from the tables, the corrosion of the test pieces was prevented by adjusting the composition of the liquid in the carbonylation reactor to specific components and specific proportions. In particular, the corrosion of the test pieces made of a corrosive metal (such as HB2) was significantly inhibited. Moreover, in the flash distillation step, the concentration of hydrogen iodide in the liquid catalyst mixture was maintained at less than 1% by weight: 0.4% by weight for Example 1, 0.4% by weight for Example 2, 0.1% by weight for Example 3, 0.4% by weight for Example 4, 0.4% by weight for Example 5, 0.4% by weight for Example 6, 0.1% by weight for Example 7, 0.1% by weight for Example 8, and 0.15% by weight for Example 9.

INDUSTRIAL APPLICABILITY

The production process of the present invention is extremely useful as a process for producing acetic acid while efficiently inhibiting the production or increased concentration of hydrogen iodide in the carbonylation reactor.

DESCRIPTION OF REFERENCE NUMERALS

1 . . . Reactor
2 . . . Flasher (evaporator)
3 . . . First distillation column
4 . . . Second distillation column
5, 6, 7, 8, 9 . . . Condenser or heat exchanger
10 . . . Scrubber system

The invention claimed is:

1. A process for producing acetic acid, which comprises a reaction step for continuously allowing methanol to react with carbon monoxide in the presence of a catalyst system comprising a metal catalyst, an ionic iodide, and methyl iodide in a carbonylation reactor,
wherein, in the reaction step, the concentration of the metal catalyst is maintained at 900 to 3000 ppm on the basis of weight, the concentration of water is maintained at 0.8 to 15% by weight, the concentration of methyl iodide is maintained at not more than 13.9% by weight, and the concentration of methyl acetate is maintained at 0.6 to 3.9% by weight, in a whole liquid phase in the reactor.

2. A process according to claim 1, wherein the production rate of acetic acid is not less than 10 mol/L·h.

3. A process according to claim 1, wherein the production rate of acetic acid is not less than 19 mol/L·h.

4. A process according to claim 1, wherein, in the liquid phase in the reactor, the concentration of the metal catalyst is maintained at 900 to 3000 ppm on the basis of weight, the concentration of water is maintained at 0.8 to 15% by weight, the concentration of the ionic iodide is maintained at not more than 25% by weight, and the concentration of methyl iodide is maintained at 2 to 13.9% by weight.

5. A process according to claim 1, wherein the production rate of acetic acid is 10 to 45 mol/L·h, and in the liquid phase in the reactor, the concentration of the metal catalyst is maintained at 900 to 3000 ppm on the basis of weight, the concentration of water is maintained at 1 to 10% by weight, the concentration of the ionic iodide is maintained at 0.5 to 25% by weight, the concentration of methyl iodide is maintained at 4 to 13.5% by weight, and the concentration of methyl acetate is maintained at 1.8 to 3.9% by weight.

6. A process according to claim 1, wherein the production rate of acetic acid is 19 to 35 mol/L·h, and in the liquid phase in the reactor, the concentration of the metal catalyst is maintained at 900 to 1500 ppm on the basis of weight, the concentration of water is maintained at 1.5 to 9% by weight, the concentration of the ionic iodide is maintained at 2 to 20% by weight, the concentration of methyl iodide is maintained at 6 to 13% by weight, and the concentration of methyl acetate is maintained at 1.8 to 3.9% by weight.

7. A process according to claim 1, wherein the reaction is conducted while maintaining a carbon monoxide pressure of not less than 900 kPa and a hydrogen pressure of not less than 4 kPa in the reactor.

8. A process according to claim 1, which further comprises a flash distillation step for continuously feeding a flasher with a reaction mixture from the reactor to evaporate a volatile component by a flash distillation, the volatile component at least containing product acetic acid, methyl acetate, and methyl iodide, and
an acetic acid collection step for separating a stream containing acetic acid from the volatile component and collecting acetic acid, wherein, in the flash distillation step, the reaction mixture is separated into the volatile component and a liquid catalyst mixture at least containing the metal catalyst and the ionic iodide, and the concentration of hydrogen iodide is maintained at not more than 1% by weight on the basis of weight in the liquid catalyst mixture.

9. A method for inhibiting corrosion of a carbonylation reactor in a production process of acetic acid, the production process comprising a reaction step for continuously allowing methanol to react with carbon monoxide in the presence of a catalyst system comprising a metal catalyst, an ionic iodide, and methyl iodide in the carbonylation reactor, wherein, in the reaction step, the concentration of the metal catalyst is maintained at 900 to 3000 ppm on the basis of weight, the concentration of water is maintained at 0.8 to 15% by weight, the concentration of methyl iodide is maintained at not more than 13.9% by weight, and the concentration of methyl acetate is maintained at 0.6 to 3.9% by weight, in a whole liquid phase in the reactor.

10. A process or method according to claim 1, wherein the material of the carbonylation reactor comprises a nickel-based alloy.

\* \* \* \* \*